(12) United States Patent
Bartlett

(10) Patent No.: US 8,021,390 B2
(45) Date of Patent: *Sep. 20, 2011

(54) APPARATUS AND METHOD FOR ANCHORING SUTURES

(76) Inventor: Edwin C. Bartlett, Greenville, NC (US)

( * ) Notice: Subject to any disclaimer, the term of this patent is extended or adjusted under 35 U.S.C. 154(b) by 707 days.

This patent is subject to a terminal disclaimer.

(21) Appl. No.: 11/638,308

(22) Filed: Dec. 13, 2006

(65) Prior Publication Data
US 2007/0162074 A1 Jul. 12, 2007

Related U.S. Application Data

(63) Continuation of application No. 10/811,691, filed on Mar. 29, 2004, now Pat. No. 7,217,280, which is a continuation of application No. 10/107,943, filed on Mar. 25, 2002, now Pat. No. 6,749,620, which is a continuation of application No. 09/712,062, filed on Nov. 14, 2000, now abandoned, which is a continuation of application No. 09/265,022, filed on Mar. 9, 1999, now Pat. No. 6,146,408, which is a continuation of application No. 08/851,583, filed on May 5, 1997, now Pat. No. 5,879,372, which is a continuation of application No. 08/308,286, filed on Sep. 19, 1994, now Pat. No. 5,626,612, and a continuation-in-part of application No. 08/124,163, filed on Sep. 20, 1993, now Pat. No. 5,540,718.

(51) Int. Cl.
*A61B 17/04* (2006.01)
*A61F 2/08* (2006.01)

(52) U.S. Cl. ........................................................ 606/232

(58) Field of Classification Search .................. 606/232, 606/132, 72, 73, 139; 623/13.14; 128/898
See application file for complete search history.

(56) References Cited

U.S. PATENT DOCUMENTS

| 1,538,173 A | 5/1925 | Daughaday |
| 2,112,337 A | 3/1938 | Gillespie |
| 3,254,890 A | 6/1966 | Watson |

(Continued)

FOREIGN PATENT DOCUMENTS
CA 2045903 1/1992
(Continued)

OTHER PUBLICATIONS

Carpenter et al., Pull-Out Strength Of Five Suture Anchors, The Journal Of Arthoscopic And Related Surgery, Feb. 1993, 109-113, 9-1.

(Continued)

*Primary Examiner* — Vy Q Bui
(74) *Attorney, Agent, or Firm* — Pandiscio & Pandiscio

(57) ABSTRACT

A suture anchor having a conical surface and a bore in which an end of an insertion tool is inserted. The insertion end of the insertion tool is made of material having elastic properties. The bore and base of the suture anchor are angled with respect to the central axis of the suture anchor and preferably are parallel to each other. During insertion, the suture anchor is reoriented to fit into the hole, thereby bending the elastic end of the insertion tool. When the suture anchor is within cancellous bone tissue, the elastic properties of the insertion tool deploys the suture anchor to an orientation in which the suture anchor cannot fit through the bone hole, thereby firmly anchoring the suture anchor in the human bone.

4 Claims, 12 Drawing Sheets

U.S. PATENT DOCUMENTS

| | | |
|---|---|---|
| 3,907,289 A | 9/1975 | Bondu, Sr. |
| 3,973,277 A | 8/1976 | Semple et al. |
| 4,386,971 A | 6/1983 | Melton et al. |
| 4,404,025 A | 9/1983 | Mercier et al. |
| 4,502,896 A | 3/1985 | Duerig et al. |
| 4,505,767 A | 3/1985 | Quin |
| 4,524,765 A | 6/1985 | de Zbikowski |
| 4,533,411 A | 8/1985 | Melton |
| 4,553,543 A | 11/1985 | Amarasinghe |
| 4,565,589 A | 1/1986 | Harrison |
| 4,605,414 A | 8/1986 | Czajka |
| 4,632,100 A | 12/1986 | Somers et al. |
| 4,669,473 A | 6/1987 | Richards et al. |
| 4,669,725 A | 6/1987 | Taylor |
| 4,678,470 A | 7/1987 | Nashef et al. |
| 4,702,250 A | 10/1987 | Ovil et al. |
| 4,738,255 A | 4/1988 | Goble et al. |
| 4,741,330 A | 5/1988 | Hayhurst |
| 4,832,026 A | 5/1989 | Jones |
| 4,898,156 A | 2/1990 | Gatturna et al. |
| 4,899,743 A | 2/1990 | Nicholson et al. |
| 4,932,973 A | 6/1990 | Gendler |
| 4,946,468 A | 8/1990 | Li |
| 4,950,296 A | 8/1990 | McIntyre |
| 4,968,315 A * | 11/1990 | Gatturna .................. 606/139 |
| 4,968,316 A | 11/1990 | Hergenroeder |
| 5,002,550 A | 3/1991 | Li |
| 5,011,473 A | 4/1991 | Gatturna |
| 5,041,129 A | 8/1991 | Hayhurst et al. |
| 5,046,513 A | 9/1991 | Gatturna et al. |
| 5,067,962 A | 11/1991 | Campbell et al. |
| 5,073,373 A | 12/1991 | O'Leary et al. |
| 5,100,417 A | 3/1992 | Cerier et al. |
| 5,102,421 A | 4/1992 | Anspach, Jr. |
| 5,112,354 A | 5/1992 | Sires |
| 5,141,520 A | 8/1992 | Goble et al. |
| 5,156,616 A | 10/1992 | Meadows et al. |
| 5,174,087 A | 12/1992 | Bruno |
| 5,176,682 A | 1/1993 | Chow |
| 5,179,915 A | 1/1993 | Cohen et al. |
| 5,192,303 A * | 3/1993 | Gatturna et al. ............. 606/232 |
| 5,203,787 A | 4/1993 | Noblitt et al. |
| 5,207,679 A | 5/1993 | Li |
| 5,211,647 A | 5/1993 | Schmieding |
| 5,217,486 A | 6/1993 | Rice et al. |
| 5,224,946 A | 7/1993 | Hayhurst et al. |
| 5,258,016 A | 11/1993 | Dipoto et al. |
| 5,269,809 A | 12/1993 | Hayhurst et al. |
| 5,290,558 A | 3/1994 | O'Leary et al. |
| 5,298,254 A | 3/1994 | Prewett et al. |
| 5,312,438 A | 5/1994 | Johnson |
| 5,354,298 A | 10/1994 | Lee et al. |
| 5,403,348 A * | 4/1995 | Bonutti .................. 606/232 |
| 5,417,712 A | 5/1995 | Whittaker et al. |
| 5,423,860 A | 6/1995 | Lizardi et al. |
| 5,439,684 A | 8/1995 | Prewett et al. |
| 5,464,425 A | 11/1995 | Skiba |
| 5,492,697 A | 2/1996 | Boyan et al. |
| 5,505,735 A | 4/1996 | Li |
| 5,540,718 A | 7/1996 | Bartlett |
| 5,554,171 A | 9/1996 | Gatturna et al. |
| 5,683,418 A | 11/1997 | Luscombe et al. |
| 5,733,306 A * | 3/1998 | Bonutti .................. 606/232 |
| 5,741,330 A * | 4/1998 | Brauker et al. ............. 424/423 |
| 5,782,863 A | 7/1998 | Bartlett |
| 5,871,503 A | 2/1999 | Bartlett |
| 5,891,150 A | 4/1999 | Chan |
| 5,961,538 A | 10/1999 | Pedlick et al. |
| 5,989,252 A | 11/1999 | Fumex |
| 6,544,281 B2 * | 4/2003 | ElAttrache et al. ........... 606/232 |
| 6,923,823 B1 | 8/2005 | Bartlett et al. |
| 2006/0036283 A1 | 2/2006 | Bartlett et al. |

FOREIGN PATENT DOCUMENTS

| | | |
|---|---|---|
| CA | 2046010 | 1/1992 |
| CA | 2159295 | 3/1996 |
| EP | 0684013 | 11/1995 |
| WO | WO 93/09730 | 5/1993 |

OTHER PUBLICATIONS

Wolf, Arthoscopic Capsulolabral Repair Using Suture Anchors, Orthopedic Clinics Of North America, Jan. 1993, 59-69, 24-1.

Richmond et al., Modification Of The Bankart Reconstruction With A Suture Anchor, The American Journal Of Sports Medicine, 1991, 343-346, 19-4.

Shirai et al., Mitsubishi Technical Bulletin, 1988, pp. 106, 184.

* cited by examiner

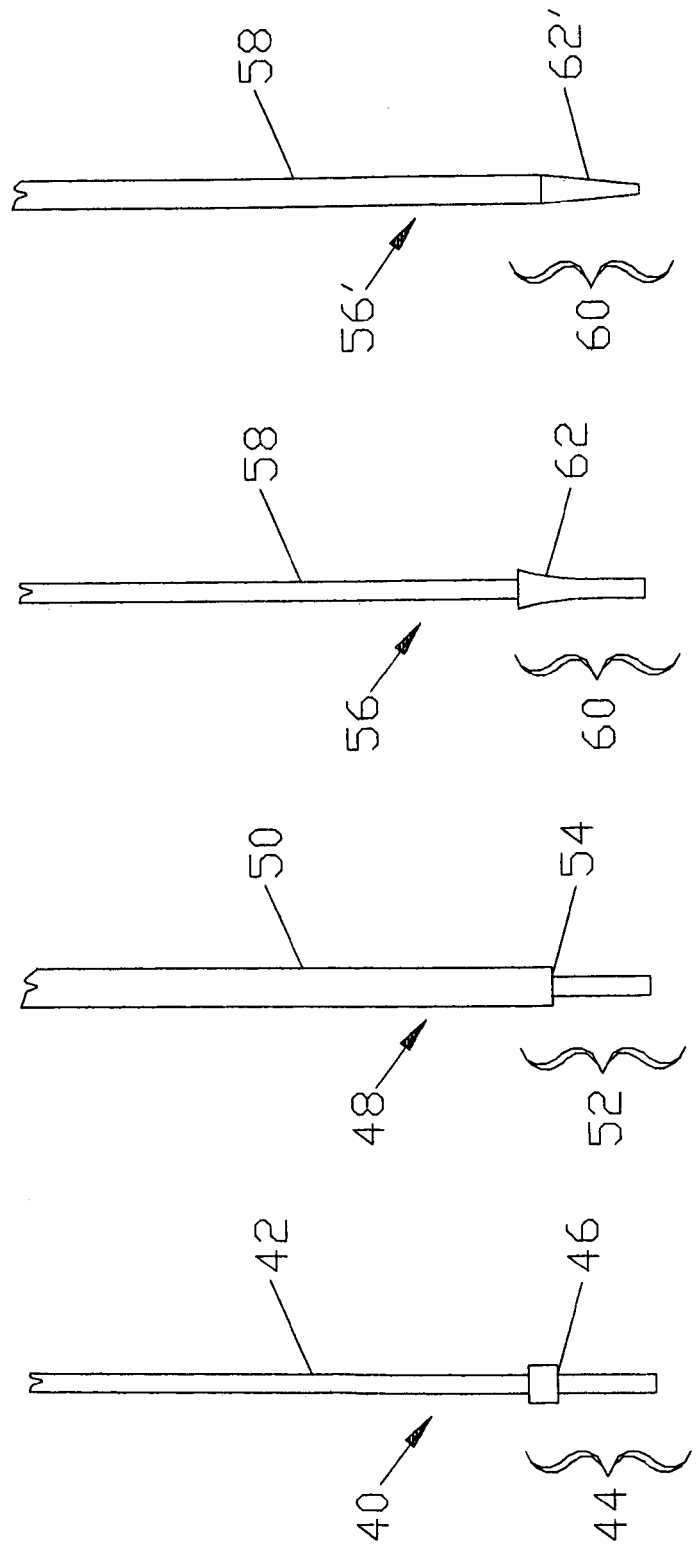

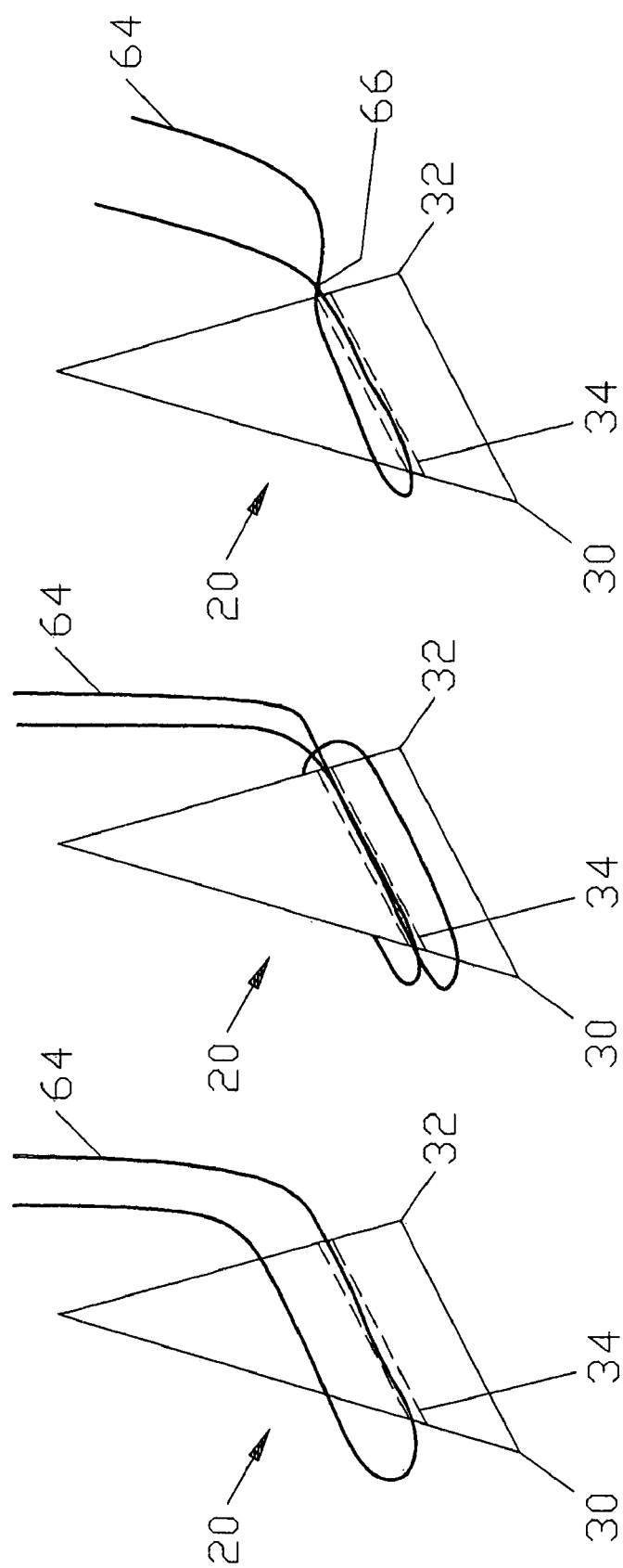

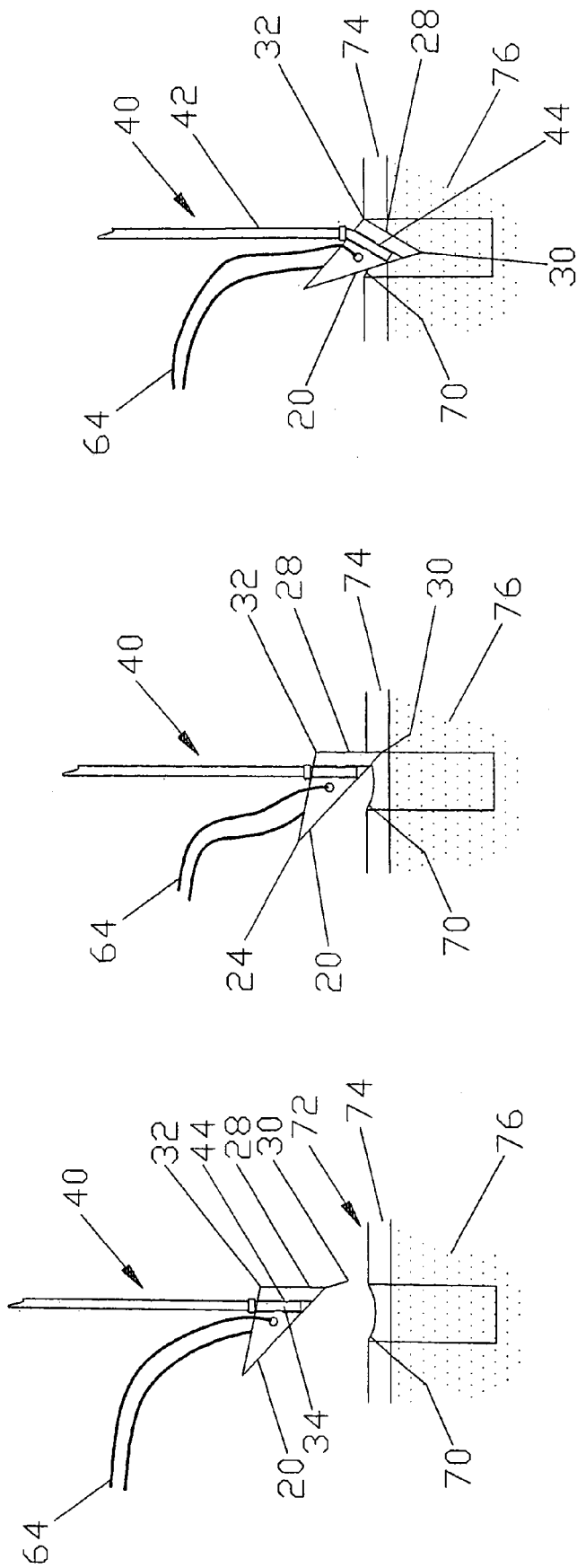

APPARATUS AND METHOD FOR ANCHORING SUTURES

REFERENCE TO PENDING PRIOR PATENT APPLICATIONS

This patent application is a continuation of prior U.S. patent application Ser. No. 10/811,691, filed Mar. 29, 2004 now U.S. Pat. No. 7,217,280 by Edwin C. Bartlett for APPARATUS AND METHOD FOR ANCHORING SUTURES, which is itself a continuation of prior U.S. patent application Ser. No. 10/107,943, filed Mar. 25, 2002 now U.S. Pat. No. 6,749,620 by Edwin C. Bartlett for APPARATUS AND METHOD FOR ANCHORING SUTURES, which is itself a continuation of prior U.S. patent application Ser. No. 09/712,062, filed Nov. 14, 2000 now abandoned by Edwin C. Bartlett for APPARATUS AND METHOD FOR ANCHORING SUTURES, which is itself a continuation of prior U.S. patent application Ser. No. 09/265,022, filed Mar. 9, 1999 now U.S. Pat. No. 6,146,408 by Edwin C. Bartlett for APPARATUS AND METHOD FOR ANCHORING SUTURES, which is itself a continuation of prior U.S. patent application Ser. No. 08/851,583, filed May 5, 1997 now U.S. Pat. No. 5,879,372 by Edwin C. Bartlett for APPARATUS AND METHOD FOR ANCHORING SUTURES, which is itself (i) a continuation of prior U.S. patent application Ser. No. 08/308,286, filed Sep. 19, 1994 now U.S. Pat. No. 5,626,612 by Edwin C. Bartlett for APPARATUS AND METHOD FOR ANCHORING SUTURES and (ii) a continuation-in-part of prior U.S. patent application Ser. No. 08/124,163, filed Sep. 20, 1993 now U.S. Pat. No. 5,540,718 by Edwin C. Bartlett for APPARATUS AND METHOD FOR ANCHORING SUTURES.

The above-identified patent applications are hereby incorporated herein by reference.

BACKGROUND OF THE INVENTION

This invention relates to an apparatus and method for anchoring sutures to a live human bone. More particularly, this invention relates to a suture anchor made of a substantially rigid, preferably biocompatible material, and most preferably a material that can be incorporated into the bone as a bone graft, such as bone, and an insertion tool having a portion made of a material having elastic properties which is inserted into the anchor and functions to orient the suture anchor, once inserted in the bone, to securely anchor the suture.

Suture anchors for anchoring a suture to bone so that another body tissue, such as muscle or ligament, may be sutured to the bone are known in the art. Such suture anchors come in a variety of shapes and designs. A survey of such suture anchors may be found in James E. Carpenter et al., "Pull-Out Strength of Five Suture Anchors", *Arthroscopy*, 9(1), pp. 109-113 (1993).

For example, harpoon-type or screw-type suture anchors are drilled into cortical bone. Examples of such suture anchors are shown, for example, in Cerrier et al. U.S. Pat. No. 5,100,417 and Hayhurst et al. Canada Patent No. 2,045,903. Such suture anchors are held in place in any of a variety of manners, such as through self-tapping, by a force fit, or by including a resilient portion which flexes to frictionally engage the bone material.

Another type of suture anchor includes a rigid member and a resilient, shape memory member. The resilient member is substantially flush with the rigid member during insertion, and flexes away from the rigid member once lodged inside the bone. Such anchors have been described in Gatturna et al. U.S. Pat. Nos. 5,046,513 and 5,192,303. The shape memory material may be made in accordance with, for example, Quin U.S. Pat. No. 4,505,767 or Harrison U.S. Pat. No. 4,565,589. Because two different materials are used, this type of suture anchor can be costly and difficult to manufacture. Moreover, the joining of two dissimilar metals leads to potential flaws and potential breakage at the joint or weld point.

A third type of suture anchor is substantially elongated and is inserted with its longitudinal axis substantially parallel to the bone hole through which it is inserted. The suture anchor is then reoriented upon reaching cancellous bone tissue by pulling on the suture attached at a selected point along the suture anchor. Examples of such suture anchors are shown in Hayhurst et al. U.S. Pat. No. 5,041,129 ("Hayhurst") and Noblitt et al. U.S. Pat. No. 5,203,787 ("Noblitt"). The Hayhurst suture anchor has a substantially cylindrical rigid body with a central bore and a longitudinal slot extending from one end to approximately the middle of the rigid body. A suture is positioned inside the central bore, and the anchor is inserted with the slot entering the bone last. Once the anchor is properly positioned, the suture is pulled through the slot towards the base of the slot, thereby reorienting the suture anchor to fix the anchor in the bone. The Noblitt suture anchor has an offset portion at which a suture is attached. Once the suture anchor is within cancellous tissue, the suture is pulled, thereby reorienting the suture anchor so that its longitudinal axis is substantially transverse to the bone hole through which it was inserted. One disadvantage associated with this type of anchor is that tugging on the suture to reorient the anchor may put undue stress on the suture (particularly at the base of the slot in Hayhurst). Moreover, the only means provided by Hayhurst and Noblitt for reorienting or deploying the suture anchor is by pulling on the suture that extends from the bone hole after insertion of the suture anchor. Furthermore, the introduction technique is unduly complicated, requiring several types of insertion tools. It is believed that inserting and seating the Noblitt suture anchor may present additional technical difficulties because of the portion of the suture anchor which is offset from the central portion of the elongated body.

A disadvantage common to all of the above-described suture anchors is that many are typically formed of metal which may not be biocompatible. Additionally, such suture anchors are typically visible during X-ray, magnetic resonance imaging (MRI), and computerized tomography (CT) examinations. Accordingly, these suture anchors may interfere with noninvasive examinations of the treated area. Moreover, the above-described suture anchors typically require complex insertion tools, the use of which is time consuming. There is thus greater potential for later complications such as bone weakening.

Two other anchoring means are staples and cement. The former is generally not desirable because staples can crack the bone in which they are inserted or damage the tissue to be connected to the bone. The latter is generally not desirable because of substance compatibility, the need for particular surface characteristics for adequate bonding, and excessive setting times.

It therefore would be desirable to provide an apparatus for anchoring a suture to a bone which is simple to manufacture and to insert, which does not interfere with noninvasive examinations such as radiographs, MRI, or CT, and which is biocompatible and most preferably, capable of being incorporated into the bone as a bone graft, to strengthen the bone. Additionally, the apparatus may be bioabsorbable.

It would also be desirable to provide a method and apparatus for inserting and deploying a suture anchor which results in a minimal number of insertion steps and requires a minimal number of tools.

SUMMARY OF THE INVENTION

It is an object of this invention to provide a suture anchor which is simple and inexpensive to manufacture and easy to insert, as well as a method of inserting and deploying the suture anchor which is relatively straightforward having a minimal number of steps, requiring a minimal number of insertion tools. Such a system for anchoring a suture to bone reduces later complications such as bone weakening.

It is also an object of this invention to provide a suture anchor which does not interfere with noninvasive examinations such as by radiographs, MRI, or CT, and is biocompatible, thus potentially causing bone strengthening after implantation. Additionally, the suture anchor may be formed from a bioabsorbable material.

These and other objects of the invention are accomplished in accordance with the principles of this invention by providing a substantially rigid suture anchor, preferably made of bone, which is reoriented after insertion to be securely positioned inside a bone. A single insertion tool pushes the suture anchor through a previously drilled hole in the bone. The insertion tool includes at least a portion made of shape memory material which is deformed during insertion of the suture anchor but which returns to its initial configuration or shape when the suture anchor is able to rotate (e.g., when in cancellous bone tissue), thereby reorienting and deploying the suture anchor to be securely positioned in the bone.

BRIEF DESCRIPTION OF THE DRAWINGS

The above and other objects and advantages of the invention, its nature, and various features will be more apparent from the following detailed description of the preferred embodiments, taken in conjunction with the accompanying drawings (in which like reference characters represent like elements throughout), and in which:

FIG. 9 is a side view of an insertion tool in accordance with the principles of this invention;

FIG. 10 is a side view of an alternative embodiment of an insertion tool in accordance with the principles of this invention;

FIG. 11 is a side view of another alternative embodiment of an insertion tool in accordance with the principles of this invention;

FIG. 12 is a side view of a modified version of the insertion tool of FIG. 11 in accordance with the principles of this invention;

FIG. 13 is a side view of a suture threaded through the suture anchor of the present invention;

FIG. 14 is a side view of an alternative manner of threading a suture through the suture anchor of the present invention;

FIG. 15 is a side view of another alternative manner of threading a suture through the suture anchor of the present invention;

FIG. 16 is a side view of a suture anchor mounted on an insertion tool and carrying a suture, in preparation for insertion into a bone;

FIG. 17 is a side view of a suture anchor mounted on an insertion tool and in the initial stages of insertion into a bone;

FIG. 18 is a side view of a suture anchor mounted on an insertion tool, shown once insertion into a bone has begun;

DETAILED DESCRIPTION OF THE INVENTION

Suture anchors constructed in accordance with the principles of the present invention are shown in FIGS. 1-8. Suture anchors 20, 22, 322, 522, and 722, which represent preferred embodiments of the present invention, are formed from a material which is biocompatible. Preferably, the selected material strengthens the bone in which the anchor is inserted. Additionally, it is desirable for the selected material to be transparent or translucent to noninvasive examinations such as by radiograph (e.g., X-ray). Accordingly, the most preferred material for the suture anchor of the present invention is cortical bone. The suture anchor of the present invention is preferably formed from strips of cortical bone cut from the midshaft of a human femur. Autologous bone can be used, but can be difficult to obtain. Allogeneic cortical bone is the preferred material, however, the use of xenogeneic cortical bone tissue is also contemplated. The suture anchor of the present invention may also be formed of a suitable biocompatible metal, polymer, or other suitable material, such as polyethylene, polymethylmethacrylate, polysulfone, and similar polymers, preferably polysulfone. Such metals, polymers, and other materials should preferably be recognized by the appropriate regulatory authority as being suitable for use in humans. Additionally, one of a variety of known bioabsorbable materials, such as polylactic acid, polydioxanone (Ethicon PDS, Ethicon Inc., Somerville, N.J.), polyglycolic acid and similar materials, or blends thereof, may be used. It will be appreciated that the biocompatible material may include suitable bioactive materials, such as hydroxyapatite or tricalcium phosphate, or suitable bioinert materials, such as alumina or zirconia.

Figure 7:
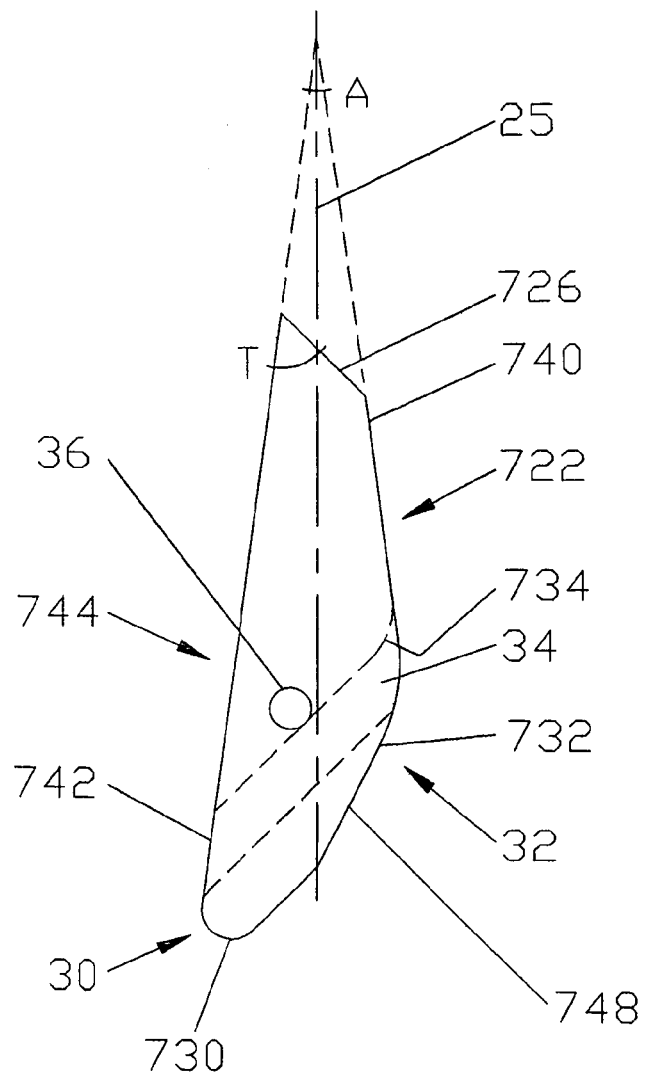
FIG. 7 is a side view of a suture anchor similar to the suture anchors of FIGS. 2-6, but having two conical surfaces with their apexes pointed away from each other in accordance with the principles of this invention.
Figure 8:
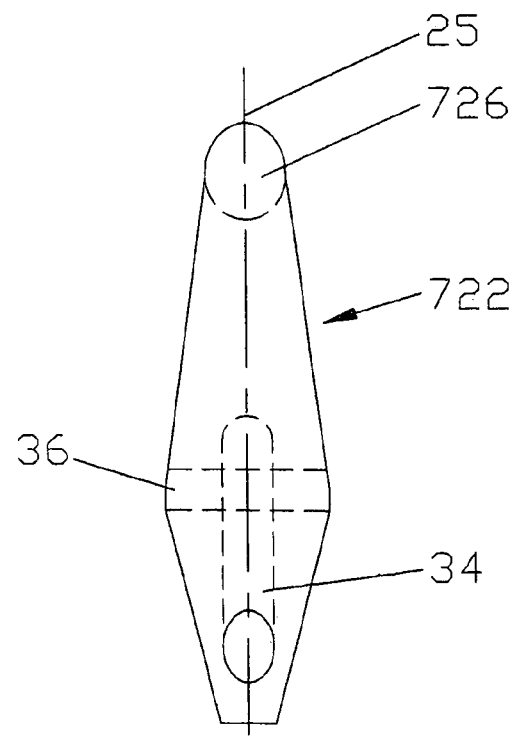
FIG. 8 is another side view of the suture anchor of FIG. 7 rotated 90° about its central axis.

Although the suture anchor of the present invention may be of any desirable elongated shape, such as a cylinder, the suture anchor of the present invention preferably has at least one generally conical surface. The term "conical surface" is to be understood in its usual sense as all or a portion of the surface generated by a moving line intersecting a fixed curve referred to as the directrix and a fixed point referred to as the vertex or apex. Thus, the suture anchor of the present invention may be a cone (FIG. 1), a truncated cone (FIGS. 2-4) such as a frustum (FIG. 2), a cone and cylinder combination (FIGS. 5 and 6), or a two cone combination (FIGS. 7 and 8). The "central axis" is the line between the apex of the cone and the center of the fixed curve that forms the directrix of the cone. In a right cone, the directrix makes a 90° angle with the plane of the directrix. One of the simplest embodiments of the invention would be a cone in which the base of the suture anchor and the directrix were the same. In the preferred embodiment shown in FIG. 1, the base of the suture anchor is cut oblique to the directrix.

The conical surfaces of the suture anchors shown in FIGS. 1-8 are all derived from right circular conical surfaces. However, the present invention also contemplates suture anchors that have a general conical surface that deviates from that of a right circular conical surface whether in the angle formed by the central axis and the directrix, such as an oblique conical surface, or in the shape of the directrix, such as an elliptical conical surface or a rhomboid conical surface. In such embodiments, it would be obvious to one of skill in the art to apply the principles set forth herein to produce a suture anchor that would function in accordance with the method of the present invention.

The length and diameter of the suture anchor are selected to provide the strongest suture anchor which can fit through the patient bone hole in which the suture anchor is to be positioned, and which can accommodate the suture required for the particular operation.

The apex angle is commonly determined first. The apex angle of suture anchors 20 and 22 is preferably approximately 20°. Thus, for suture anchors 20 and 22, central axis 25 forms an approximately 10° angle with the conical surface 40. This is shown for suture anchors 20 and 22 in FIGS. 1 and 2 respectively. The apex angle A of suture anchors 322, 522 and 722 is preferably approximately 15°. Thus, for suture anchors 322, 522 and 722, central axis 25 preferably forms an approximately 7.5° angle with conical surfaces 340, 540 and 740, respectively. This is shown for suture anchors 322, 522 and 722 in FIGS. 3, 5 and 7, respectively.

The length of the suture anchors 20, 22, 322, and 722 is preferably approximately 0.455 in. (1.156 cm). The length of suture anchor 522 is preferably approximately 0.440 in. (1.118 cm).

The thickest diameter of suture anchors 20, 22, 322, and 722 is preferably approximately 0.117 in. (0.297 cm). The diameter of the cylindrical portion of suture anchor 522 is preferably approximately 0.113 in. (0.287 cm). The size of the patient bone hole through which the suture anchor is inserted is within the range of 1-12 mm, typically within 2-6 mm.

Preferably, the patient bone hole is within 2.5-3.5 mm. The patient bone hole is formed according to any desired method, utilizing any suitable means. It should be appreciated that the optimum shape and size of the suture anchor may vary according to the site of use in the patient. One of ordinary skill in the art could determine, by routine experimentation, the optimum shape and size of the suture anchor for a particular application at a particular site of use.

Figure 1:
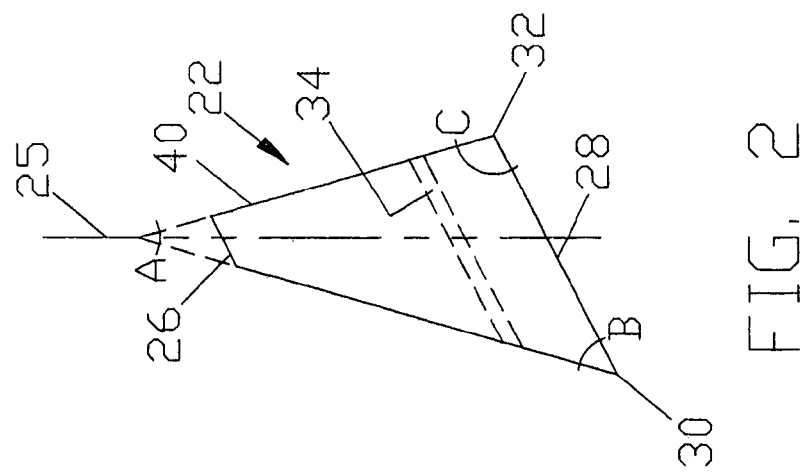
FIG. 1 is a side view of a suture anchor having a conical surface in accordance with the principles of this invention.

Suture anchor 20 of FIG. 1 is a cone with apex 24. Such a suture anchor may be described as having a first conical surface 40, a base 28 closing off the open end of the conical surface, a central axis 25, and an anchor bore 34 across the conical surface.

A conical suture anchor may easily be formed by inserting an end of a strip of the desired material into a milling, turning or other suitable cutting or shaping device. Such devices are well known in the art. For example, a mill may be designed for shaping bone or other materials in accordance with the principles of a common pencil sharpener. Alternatively, the suture anchor may be formed by casting, molding or any other suitable method.

Apex 24, or a portion thereof, is useful for cutting through cancellous bone tissue once suture anchor 20 passes through the cortical bone tissue. Angle A of apex 24 is selected to efficiently cut through cancellous bone tissue and can range from 10°-60°. Preferably, apex angle A is between 10°-20°. The exact angle will depend on the apparatus used, and most typically is approximately 15°-20°.

Figure 2:
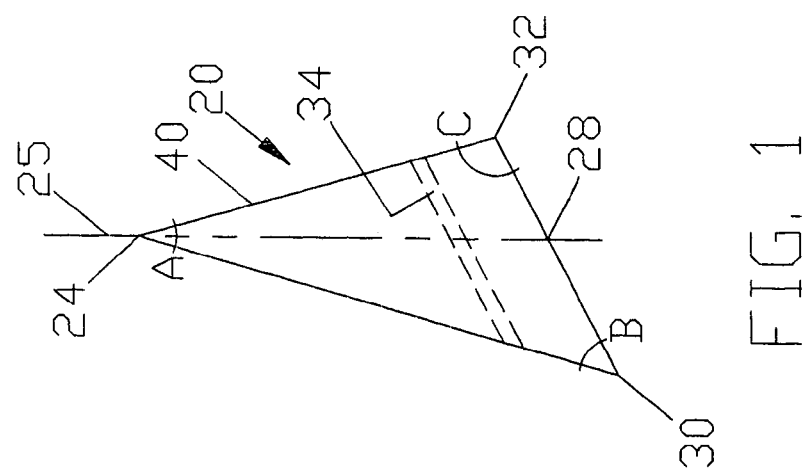
FIG. 2 is a side view of a modified suture anchor similar to the suture anchor of FIG. 1, but with truncated apex in accordance with the principles of this invention.
Figure 3:
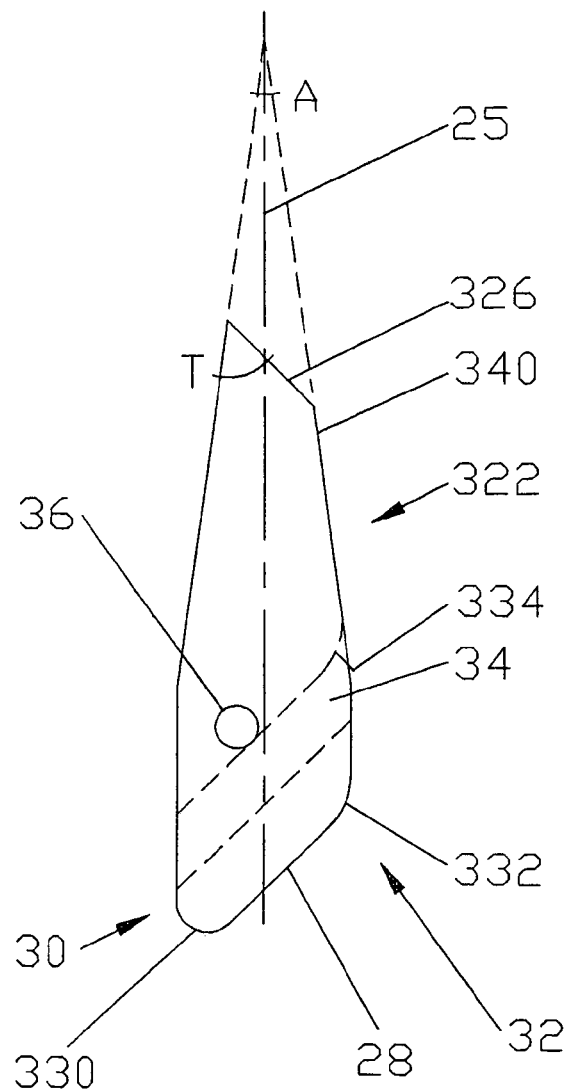
FIG. 3 is a side view of a suture anchor similar to the suture anchor of FIG. 2, but with rounded edges, in accordance with the principles of this invention.

For greater strength in the apical area, it may be desirable to cut off the apex of the conical suture anchor to form a flattened trailing end 26 (FIG. 2), 326 (FIG. 3), 526 (FIG. 5), 726 (FIG. 7). The angle at which the apex is cut may result in a frusto-conical suture anchor 22 (FIG. 2), or a truncated conical suture anchor 322 (FIGS. 3 and 4), 522 (FIGS. 5 and 6), 722 (FIGS. 7 and 8). The amount by which the cone's apex is truncated should preferably maximize the structural strength of the apical region of the suture anchor, while retaining a general conical shape. This enables travel through cancellous bone tissue during reorientation and positioning of the suture anchor after insertion. Preferably, the apex is cut so that the trailing end formed is at an approximately 45° angle T with the conical surface to form a truncated conical suture anchor 322, 522, 722 as shown in FIGS. 3, 5, and 7.

Each of suture anchors 20, 22, 322, and 522 has a substantially planar base 28 which preferably is cut oblique (i.e., neither parallel nor perpendicular) to the central axis (the base of suture anchor 722 is a second conical section). Because base 28 is cut oblique to the central axis, the angle formed between the conical surface and the base of suture anchors 20, 22, 322, and 522 varies along the circumference of base 28. The leading bottom edge 30 (the first area of the edge of base 28 to enter the patient bone hole through which the suture anchor is to be inserted, as further described below) preferably has the smallest angle B between the conical surface and base 28. Accordingly, trailing edge 32, opposite leading edge 30, is at angle C, preferably the largest angle between the conical surface and base 28. Angles B and C are shown in FIGS. 1 and 2.

The specific angle at which base 28 is cut with respect to the central axis is determined primarily by the size of the patient bone hole, to achieve the most easily insertable suture anchor. The measurement of the angle formed by the central axis and the conical surface and the desired length of the suture anchor also affect the angle at which base 28 should be cut. The suture anchor must be sufficiently narrow, in at least one orientation, such that it is able to fit through the patient bone hole in which the suture anchor is to be positioned. Thus, when the suture anchor is inserted into the patient bone hole (with base 28 parallel to the walls of the patient bone hole) trailing edge 32 should be able to fit into the patient bone hole as well in order to ensure that the remainder of the suture anchor will be able to fit through the patient bone hole. Preferably, the widest part of the suture anchor is approximately 0.2-0.5 mm less than the patient bone hole. Preferably, base 28 is cut at an angle of approximately 45° with respect to the central axis. Typically, the resulting angle C at the trailing edge is between 90°-165°, and most preferably approximately 128°.

Each of suture anchors 20, 22, 322, 522, and 722 has an anchor bore 34 in which an insertion tool is positioned to insert the suture anchor into the patient bone hole. Preferably, as shown in FIGS. 1, 2, 3, and 5, anchor bore 34 is drilled parallel to base 28 extending generally in a direction from the trailing end toward the leading edge. It will be appreciated that bore size may vary according to the overall size of the suture anchor and the physical requirements of the insertion tool. For suture anchors that fit through an approximately 3 mm bone hole, the diameter of anchor bore 34 is preferably between 0.025-0.042 in. (0.635-1.067 mm), most preferably approximately 0.035 in. (0.889 mm). Furthermore, the anchor bore 34 of the suture anchor may be tapered to a smaller diameter as it travels toward the leading edge. Preferably, as shown in FIGS. 3, 5, and 7, the end of anchor bore 34 in which an insertion tool is inserted has a radiused area 334, 534, 734, having a radius of curvature of approximately 0.1 in. (2.54 mm). The suture may be threaded through anchor bore 34 alongside the insertion tool.

Alternatively, a separate suture accessory bore 36 (shown in FIGS. 3-8) may be formed substantially perpendicular to anchor bore 34 (FIGS. 4, 6, 8) for separately accommodating the suture. As shown in FIGS. 3, 5 and 7, preferably accessory bore 36 is located between anchor bore 34 and the apex of the suture anchor. However, it is within the scope of the present invention for the accessory bore to be located between the anchor bore and the base of the suture anchor. The diameter of the accessory bore 36 may vary according to the size and strength of suture used. For suture anchors that fit through an approximately 3 mm bone hole, accessory bore 36 preferably has a diameter between 0.019-0.030 in. (0.483-0.762 mm), most preferably approximately 0.028 in. (0.7112 mm). Bores 34 and 36 will be discussed in greater detail below in connection with the insertion tool of the present invention and the method of inserting the suture anchor in accordance with the principles of the present invention.

Figure 4:
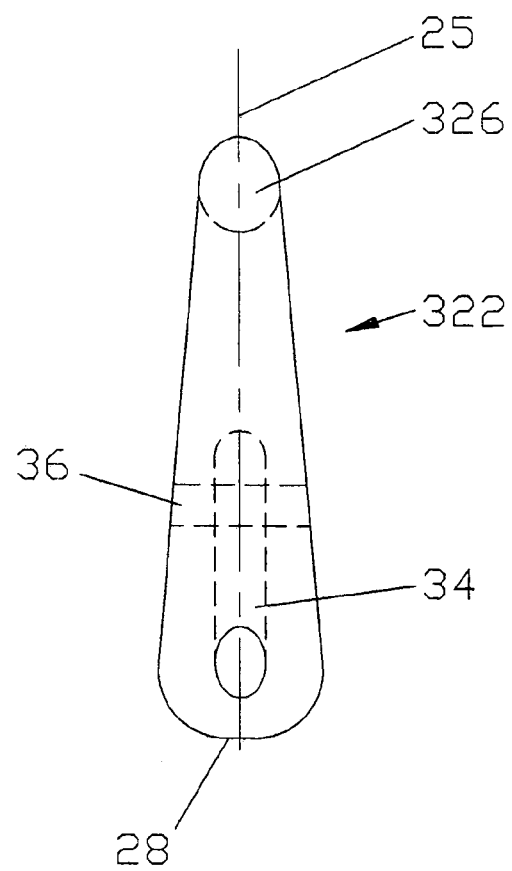
FIG. 4 is another side view of the suture anchor of FIG. 3 rotated 90° about its central axis.
Figure 5:
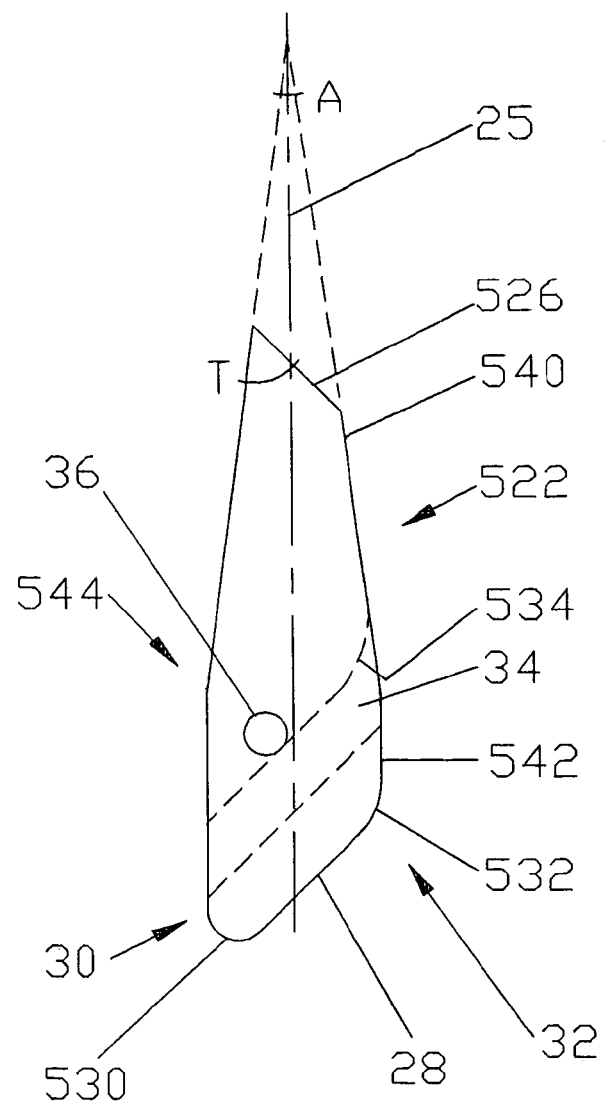
FIG. 5 is a side view of a suture anchor similar to the suture anchors of FIGS. 2-4, but having both a conical surface and a cylindrical surface in accordance with the principles of this invention.

The shape of suture anchor 322 of FIGS. 3 and 4 is substantially the same as suture anchor 22 of FIG. 2, except the edges of suture anchor 322 are radiused. Preferably, radiused area 330 of leading edge 30 has an approximately 0.02 in. (0.508 mm) radius of curvature, and radiused area 332 of trailing edge 32 has an approximately 0.12 in. (3.048 mm) radius of curvature. As shown in FIG. 3, base 28 appears mostly rounded. Similarly, suture anchor 522 also has radiused edges. Preferably, radiused area 530 has an approximately 0.02 in. (0.508 mm) radius of curvature, and radiused area 532 has an approximately 0.05 in. (1.27 mm) radius of curvature.

In order to reduce stress on the suture anchor at bores 34 and 36, suture anchors 522 and 722 are not conical past the area of bores 34 and 36, as shown in FIGS. 5-8.

Suture anchor 522 is formed with a conical surface 540 up to bores 34 and 36 and a cylindrical surface 542 extending from bores 34 and 36 to base 28. Such a suture anchor may be generally described as having a first conical surface 540, a base 28 closing off the open end of the conical surface, a central axis 25, and an anchor bore 34 across said conical surface with a cylindrical surface 542 extending between the open end of the conical surface and the base. The diameter of cylindrical surface 542 is preferably substantially equal to the diameter of conical surface 540 at transition point 544 from conical to cylindrical. Thus, provided that the suture anchors are of comparable length and apex angle, the widest part of suture anchor 522 is narrower than the widest part suture anchors 20, 22, and 322 and, accordingly, suture anchor 522 can fit in a narrower patient bone hole. Because of its strength and size, suture anchor 522 is a particularly preferred embodiment. When measured from end to end, at its largest distance, suture anchor 522 is preferably approximately 0.44 in. (1.1176 cm) in length.

Instead of having a cylindrical surface after bores 34 and 36, suture anchor 722 has a secondary conical surface 742, tapering away from bores 34 and 36 and primary conical surface 740, as shown in FIGS. 7 and 8. Such a suture may be generally described as having a first conical surface 740, a central axis 25, an anchor bore 34 across the conical surface and a base comprising a second conical surface 742 inverted with respect to the first conical surface. Accordingly, the thickest portion of suture anchor 722 is at transition point 744. Preferably, secondary conical surface 742 has a flattened area 748 adjacent to the insertion end of anchor bore 34 (the end through which the insertion tool is inserted, as described in further detail below) for added suture anchor strength in the area of the bores.

Suture anchors 20, 22, 322, 522, and 722 have an anchor bore 34 in which the insertion tool is positioned to insert the suture anchor, and also through which the suture may be threaded. The diameter of anchor bore 34 is determined by the diameter of the insertion tool to be used and, if the suture is also threaded through anchor bore 34, the suture to be anchored. Anchor bore 34 may be tapered to provide a tighter fit for the insertion tool and to increase the strength of the suture anchor (because less material is removed to create the bore). Typically, the diameter of anchor bore 34 is between $\frac{1}{32}$-$\frac{1}{16}$ inches, and most preferably 0.035 in. (0.889 mm).

Anchor bore 34 need not be cylindrical, and may have any of a variety of cross-sectional shapes. If the suture is to be threaded through anchor bore 34, the shape of anchor bore 34 preferably includes a section in which the suture can travel to minimize contact between the suture and the insertion tool during the insertion process. Potential cross-sectional shapes for anchor bore 34 thus include oblong, elliptical, tear-drop, a figure eight (thereby providing separate but connected bores for the suture and the insertion tool), substantially circular with a slot for the suture to run through, or any other shape that can accommodate the suture as described. The entry and exit areas of anchor bore 34 preferably are chamfered or radiused (see radiused areas 334, 534, 734 in FIGS. 3, 5, and 7, respectively) to reduce stress on the suture when the suture is pulled to reorient the suture anchor and during subsequent suturing. Anchor bore 34 is preferably cut at an angle oblique to the central axis. Preferably, anchor bore 34 and base 28 are parallel. However, it is within the scope of the present invention to form anchor bore 34 and base 28 at different angles with respect to the central axis. However, anchor bore 34 should be oriented such that, during the process of insertion of the suture anchor, force applied by the insertion tool advances leading edge 30 of the suture anchor toward and through the patient bone hole (as described in further detail below).

In order to minimize contact between the suture and insertion tool during the insertion process, it is preferable to thread the suture through an accessory bore 36 having a diameter of preferably approximately 0.028 in. (0.7112 mm). The use of a separate accessory bore 36 for the suture reduces stress that may be put on the suture if threaded in anchor bore 34 alongside the insertion tool. Accessory bore 36 is preferably substantially perpendicular to anchor bore 34, as seen in the side views of suture anchors 322, 522 and 722 in FIGS. 4, 6, and 8, respectively. The location of accessory bore 36 is selected to have the smallest effect on the strength of the suture anchor because of the deficit of suture anchor material. One of ordinary skill in the art can determine, by routine experimentation and an analysis of the geometry of the suture anchor, the optimum point at which accessory bore 36 can be placed without detrimentally effecting the strength of the suture anchor. The distance of accessory bore 36 from leading edge 30, along the axis of the suture anchor, is preferably between 0.15-0.20 in. (3.81-5.08 mm), and most preferably approximately 0.18 in. (4.572 mm) in suture anchors 20, 22, 322, and 722, and 0.16 in. (4.064 mm) in suture anchor 522.

In order to function properly, the insertion tool should be limited in travel through anchor bore 34 of the suture anchor. Accordingly, the insertion tool of the present invention has a means for limiting the travel of its insertion end into anchor bore 34. Examples of insertion tools having means for limiting insertion end travel are shown in FIGS. 9-12.

Insertion tool 40 of FIG. 9 has a substantially straight elongated body 42 ending with insertion end 44, which is inserted inside anchor bore 34 of the suture anchor. Bead 46 demarcates insertion end 44 from the remainder of body 42 and prevents body 42 from entering anchor bore 34. The diameter of insertion end 44 should be sufficiently wide to provide a secure fit inside anchor bore 34 of the suture anchor (also accounting for the amount of suture material, if any, inside anchor bore 34). The diameter of bead 46 should be substantially larger in diameter than anchor bore 34 in order to limit movement of insertion end 44 through anchor bore 34.

Insertion tool 48 of FIG. 10 also has a substantially straight elongated body 50 ending at insertion end 52. Like insertion tool 40, insertion end 52 of insertion tool 48, is distinctly demarcated from the remainder of body 50 to thereby limit movement of body 50 through anchor bore 34. In this instance, insertion end 52 is narrower than body 50 and distinctly begins at step 54. Insertion end 52 must be sufficiently thick to form a secure fit within anchor bore 34 of the suture anchor during insertion into the patient bone hole (also accounting for the amount of suture material, if any, inside anchor bore 34). It will be appreciated that one or both sides of insertion tool 48 may be stepped.

Insertion tool 56 of FIG. 11 has a substantially straight elongated body 58, similar to bodies 42 and 50. However, instead of having a demarcation between body 58 and insertion end 60, such as bead 46 or step 54, insertion tool 56 has a wedged end 62, with the narrowest part at the free end of insertion tool 56. The dimensions of wedge 62 are selected to securely fit within anchor bore 34 of the suture anchor (also accounting for the amount of suture material, if any, inside anchor bore 34) to hold the suture anchor during insertion into the patient bone. It will be appreciated that one or both sides of insertion tool 56 may be wedged. Insertion tool 56' of FIG. 12 is substantially the same as insertion tool 56, except wedged end 62' smoothly joins body 58, instead of extending away from body 58 into a portion wider than body 58, as does wedged end 62. Preferably, wedged end 62' tapers from about 0.062 in. (1.575 mm) down to about 0.016 in. (0.4064 mm).

Insertion tools 40, 48, 56, and 56' may have a handle (not shown) at the end opposite insertion end 44, 52, 60 to facilitate gripping of the insertion tool during insertion of the suture anchor into the patient bone hole. Typically the hand grip would be wider and longer than body 42, 50, and 58.

For reasons as will be described in connection with the method of insertion, at least insertion ends 44, 52, and 60 of insertion tools 40, 48, 56 and 56', respectively, should be formed from a material having elastic properties, preferably superelastic properties, such as a shape memory material. The elastic or superelastic properties of the material should be such that the insertion end is not substantially permanently deformed during insertion of the suture anchor and will substantially return the insertion end to an initial configuration (generally the configuration of the insertion end at the time it is initially mounted in anchor bore 34, prior to insertion of the suture anchor into the patient bone). The preferred material for at least the insertion end of the insertion tool is a nickel titanium alloy. Such materials are available commercially, under the names NITINOL™ or TINEL™ (RayChem) or SENTINOL™ (GAC International, Inc.). Such shape memory alloys having superelastic properties are well known in the art. See, e.g., U.S. Pat. Nos. 4,505,767, and 4,565,589. However, any other shape retaining material sufficient for properly inserting the suture anchor of the present invention into a patient bone hole may be used. See e.g., Shirai and Hayashi, *Mitsubishi Technical Bulletin,* 184, pp. 1-6 (1988).

Any suitable means for attaching the suture to the suture anchor may be used within the scope of the invention. Suture 64 is most preferably threaded through accessory bore 36 shown in FIGS. 3-8. However, suture 64 may instead be threaded through anchor bore 34 of the suture anchor in any preferred manner, such as those illustrated in FIGS. 13-15. For sake of simplicity, suture anchor 20 is shown in FIGS. 13-15. However, it will be understood that the discussion below relates to attaching a suture to any of the suture anchors of the present invention, including suture anchors 322, 522 and 722.

In FIG. 13, one end of suture 64 is threaded through anchor bore 34 and looped around the conical surface of suture anchor 20 adjacent leading edge 30. Thus, suture 64 passes through suture anchor 20 only once, as thread through the eye of a needle. When threaded in this manner, suture 64 can freely travel through anchor bore 34. When threaded in this manner, pulling one of the free ends of suture 64 may cause the suture anchor to rotate approximately 90°.

Suture 64 may, instead, be more fixedly threaded through anchor bore 34, as shown in FIGS. 14 and 15. In FIG. 14, suture 64 is looped over suture anchor 20, and the free ends of suture 64 are then threaded through the end of anchor bore 34 adjacent leading edge 30, exiting anchor bore 34 adjacent trailing edge 32. Suture 64 is then pulled to tighten the loop around suture anchor 20. When an end of suture 64 is pulled, suture anchor 20 will barely rotate, if at all, maintaining anchor bore 34 relatively parallel to the patient bone hole.

Suture 64 is knotted to anchor 20 in FIG. 15. As shown in FIG. 15, only one end of suture 64 is threaded through anchor bore 34 as in FIG. 13. However, upon exiting anchor bore 34, knot 66 is formed with the ends of suture 64 at the exit of anchor bore 34, preferably adjacent trailing edge 32. As in FIG. 14, the manner of threading shown in FIG. 15 may produce minimal rotation of suture anchor 20 if an end of suture 64 is pulled.

The preferred method of inserting the suture anchor of the present invention is illustrated in FIGS. 16-23. For the sake of simplicity, suture anchor 20 is shown. It will be understood that any of suture anchors 22, 322, 522, or 722 may be used in the method described below. A patient bone hole 70 has already been drilled into patient bone 72. Patient bone hole 70 extends completely through cortical bone matter 74. Patient bone hole 70 may also extend, at least partially, through cancellous bone tissue 76, preferably to a depth about equal to the length of the suture anchor. It will be understood that any insertion tool with a shape memory insertion end may be used in the preferred insertion method. Moreover, any suitable substantially rigid anchor with a bore for the insertion tool may be used. This method is illustrated schematically in FIGS. 16-23.

As shown in FIG. 16, suture 64 is threaded through anchor bore 34, and suture anchor 20 is mounted on insertion end 44 of insertion tool 40. Insertion end 44 enters anchor bore 34 adjacent trailing edge 32 of suture anchor 20 and exits (if at all) adjacent leading edge 30. Because insertion end 44 of tool 40 is securely positioned within anchor bore 34, anchor bore 34 is not easily distinguishable, in the FIGS., from the outer surface of insertion end 44. Anchor bore 34 is preferably drilled parallel to base 28 such that force applied by the insertion tool advances the leading edge of the suture anchor toward the patient bone hole. Insertion tool 40 is positioned parallel to the longitudinal axis of patient bone hole 70, maintaining anchor bore 34 and base 28 (if anchor bore 34 is drilled parallel to base 28) parallel to patient bone hole 70, as well. Leading edge 30 of suture anchor 20 is positioned to be the first portion of suture anchor 20 to enter patient bone hole 70.

Initial entry of suture anchor 20 into patient bone hole 70 is shown in FIG. 17. The conical surface extending between leading edge 30 and apex 24 has not yet encountered patient bone hole 70. As alluded to above, this portion of the conical surface of suture anchor 20 should not encounter patient bone hole 70 until trailing edge 32 also encounters patient bone hole 70.

Once the conical surface extending between leading edge 30 and apex 24 encounters patient bone hole 70, suture anchor 20 begins to rotate or reorient, as shown in FIG. 18, in order to fit into patient bone hole 70. Main body 42 of insertion tool 40 is maintained parallel to patient bone hole 70. Thus, when suture anchor 20 reorients, insertion end 44 bends.

Figure 19:
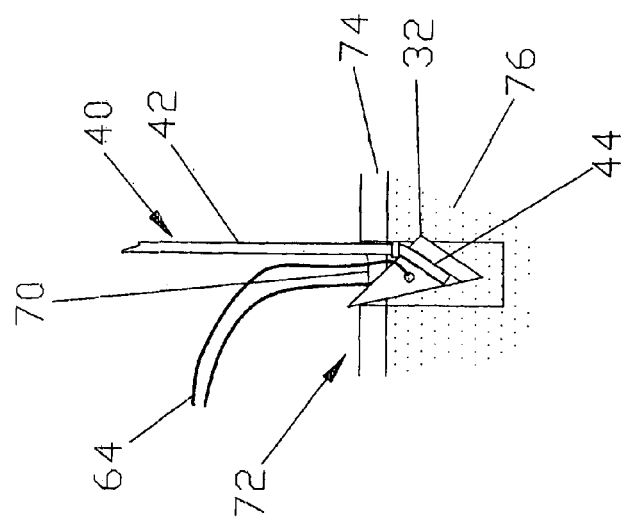
FIG. 19 is a view similar to that of FIG. 18, but shows further progress of the suture anchor and insertion tool into the bone, in the position at which the insertion tool is in its most deformed state.
Figure 20:
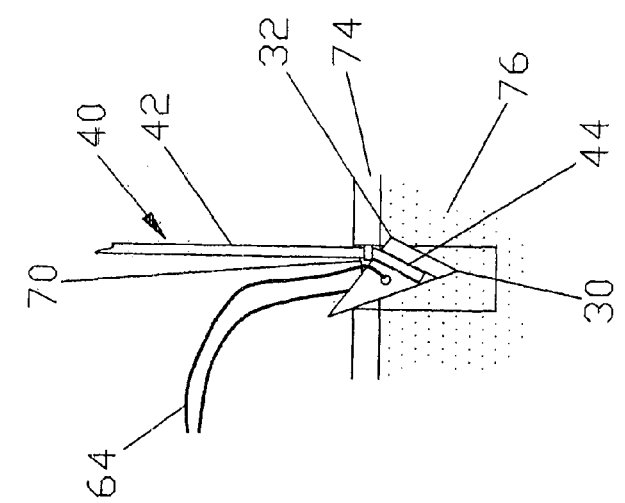
FIG. 20 is a view similar to that of FIG. 19, but shows the insertion tool beginning to resume its initial configuration.
Figure 21:
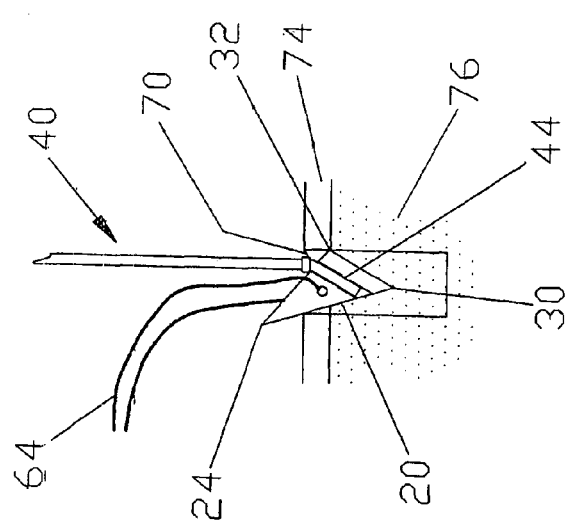
FIG. 21 is a view similar to that of FIG. 20, but shows the suture anchor almost completely inside the bone, but not yet within a secure anchoring position.

Typically, insertion end 44 is bent to the greatest extent immediately before trailing edge 32 leaves the portion of patient bone hole 70 in patient cortical bone tissue 74, as shown in FIG. 19. Once trailing edge 32 begins travelling through patient cancellous bone tissue 76, insertion end 44 begins to resume its initially straight configuration, as shown in FIGS. 20 and 21, thereby deploying the suture anchor. Preferably main body 42 of insertion tool 40 is not as flexible as insertion end 44, and remains straight throughout the insertion procedure.

Figure 23:
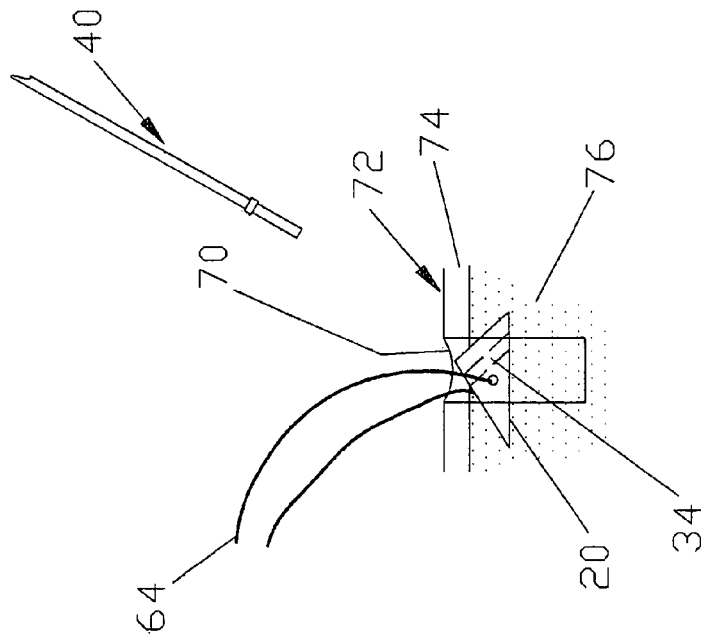
FIG. 23 is a side view of a suture anchor in a secure anchoring position, dismounted from the insertion tool.
Figure 22:
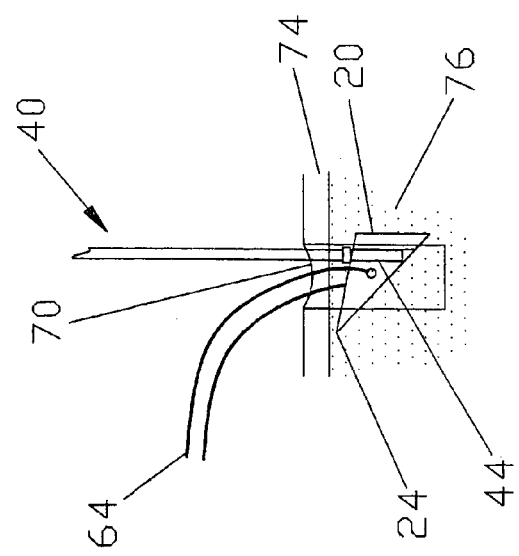
FIG. 22 is a side view of a suture anchor completely positioned in cancellous bone tissue, the suture anchor still mounted on the insertion tool, which has resumed its initial configuration.

Once apex 24 has cleared patient cortical bone tissue 74, and the entire suture anchor is in cancellous bone tissue 76, insertion end 44 of insertion tool 40 is able to return to its original configuration, as shown in FIG. 22. The pointed shape of apex 24 allows suture anchor 20 to more easily cut through cancellous bone tissue 76 so that the suture anchor may be reoriented and secured in its final position. As shown in FIG. 23, insertion tool 40 can then be disengaged from the suture anchor and removed. Pulling the suture anchor 64 up and away from patient bone 72 at this point may aid in dismounting the suture anchor from the insertion tool in addition to rotating and thereby properly seating suture anchor 20 in cancellous bone tissue 76. Preferably suture 64 is once again pulled up and away from patient bone 72 after the insertion tool is removed to firmly position suture anchor 20 in patient bone 72, preferably against the undersurface of cortical bone 74, within the transition region between cortical bone matter 74 and cancellous bone matter 76. Typically, suture 64 will be substantially centered within patient bone hole 70, and suture anchor 20 will be substantially horizontal. Suturing of body tissue to patient bone 72 can now be commenced.

EXAMPLE 1

Figure 6:
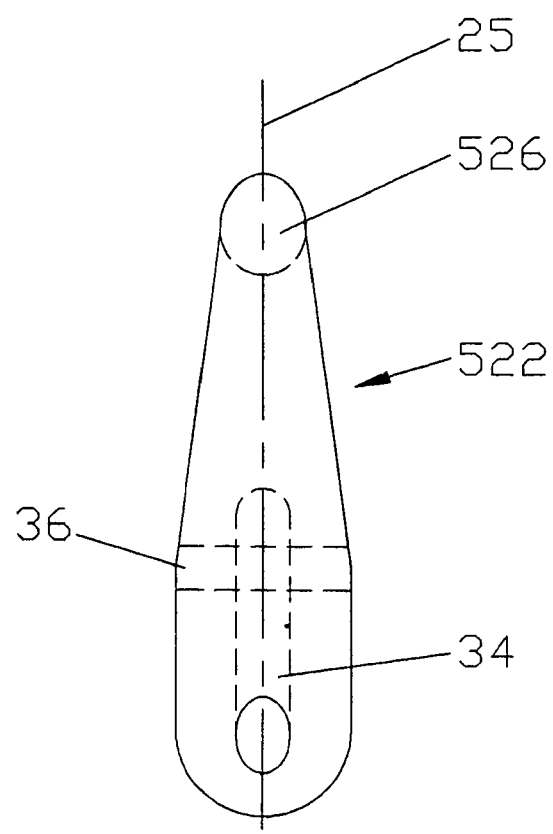
FIG. 6 is another side view of the suture anchor of FIG. 5 rotated 90° about its central axis.

Suture anchors substantially as shown in FIGS. 5 and 6, made from bony allograft, were fashioned from 4-8 mm strips of hydrated cortical bone. Initial conical shaping was done on a medium grain stone grinding wheel. The conical shape was then made uniform with a mill made from a pencil sharpener. An anchor bore and an accessory bore were then drilled using a guide jig to control size and location. Final smoothing and shaping including the cylindrical portion of the anchor was done with a dremel tool. The dimensions of the final suture anchor were as set out above for the preferred embodiment of suture anchor 522.

An insertion tool substantially as shown in FIG. 12 was shaped from 0.062 in. (1.575 mm) NITINOL™ ground to a tapered tip (using two grinding wheels on a centerless grinding tool). A handle was fashioned from a stainless steel dowel drilled to accept the body of the insertion tool.

Human cadaveric humerus and pig pelvis in which a hole of about 3 mm was drilled was used as a model to test pull-out strength of the above suture anchor. Steel wire (26 gauge) was threaded through the accessory bore of the suture anchor to assure that anchor failure rather than suture failure was tested.

The threaded suture anchor was mounted on the insertion tip of the insertion tool and advanced into the bone hole with the body of the insertion tool parallel to the longitudinal axis of the bone hole. Once the suture anchor was deployed, the insertion device was removed and the end of the stainless steel suture were tied to form a loop. The suture anchors were tested to anchor failure using a spring loaded scale with an automatic marker. Failure strength greater than 30 lbs. exceeds industry standards.

Several tests were performed. For each trial, the load at failure and the type of failure were determined. Anchor failure was defined as the suture anchor breaking. The ultimate failure strength of a suture anchor was recorded as the maximal force applied when the anchor broke. These results did not include those trials in which the anchor pulled out of the bone.

The measured failure strengths of a suture anchor formed from bony allograft was consistently measured at greater than 32 pounds. This measured failure strength far exceeds the industry standard.

EXAMPLE 2

Suture anchors substantially as shown in FIGS. 5 and 6, made of the biocompatible polymer polysulfone, were fashioned by drilling cylindrical stock polysulfone. The suture anchors were then shaped on a lathe. The bores were then radiused and the ends cut. The dimensions were as set out above for the preferred embodiment of suture anchor 522.

An insertion tool fashioned as described in Example 1 was used to implant the anchors into specimens of human humerus and pig pelvis. Several tests of suture anchor strength were performed as outlined in Example 1.

The measured failure strengths of a suture anchor formed from polysulfone was consistently measured at greater than 32 pounds. This measured failure strength far exceeds industry standards.

It will be understood that the foregoing is merely illustrative of the principles of this invention, and that various modifications can be made by those skilled in the art without departing from the scope and spirit of the invention. For example, the suture anchors and insertion tools used in the preferred insertion method (illustrated in FIGS. 16-23) may be formed in shapes other than those illustrated, but which will function in accordance with the method of the present invention. Moreover, it will be appreciated that although it is not necessary to use the insertion tools typically used during suture anchor insertion (such as cannulas), the use of such tools is contemplated within the scope of the present invention.

Thus, it will be appreciated that the scope of this invention includes all alternative embodiments and variations which are defined in the foregoing specification and by the claims appended hereto; and the invention is not to be limited by the specific embodiments that have been presented herein by way of example.

What is claimed is:

1. A method of anchoring a suture to live human bone through a substantially cylindrical bone hole having a longitudinal axis, the method comprising the steps of:
    providing an insertion tool comprising a main body and a flexible insertion end having elastic properties for returning the insertion end to an initial configuration;
    providing a substantially rigid suture anchor of human femur cortical bone having at least one generally conical surface and a central axis and a bore at an angle to the central axis, and a substantially planar base oblique to the central axis;
    securing a suture to the suture anchor by threading the suture through the bone;
    positioning the insertion end of the insertion tool through the bore;
    advancing the insertion tool towards the bone hole with the main body parallel to the longitudinal axis and the insertion end in the initial configuration, wherein the suture anchor, as oriented on the insertion end, is too large to fit through the bone hole;
    advancing the insertion tool and the suture anchor into the bone hole, causing the suture anchor to reorient by bending on the insertion end of the insertion tool; and
    advancing the insertion tool into the bone hole until the insertion tool end having elastic properties is able to return to an initial configuration, thereby reorienting the suture anchor to the orientation prior to insertion into the bone hole.

2. The method of claim 1 wherein the step of securing the suture to the suture anchor further includes the step of inserting the suture through the bore in which the insertion end is inserted.

3. The method of claim 1 wherein the suture anchor further comprises an accessory bore, and the step of securing the suture to the suture anchor further comprises the step of inserting the suture through the accessory bore.

4. The method of claim 1 further including the step of pulling the suture away from the bone hole after the suture anchor has been reoriented inside the bone hole, to thereby further secure the suture anchor in the bone hole.

* * * * *